United States Patent [19]

Catsimpoolas et al.

[11] Patent Number: 4,767,746
[45] Date of Patent: Aug. 30, 1988

[54] METHOD FOR ENHANCEMENT OF HEALING OF EPITHELIAL WOUNDS IN MAMMALS

[75] Inventors: Nicholas Catsimpoolas, Newton Centre, Mass.; Robert S. Sinn, New York, N.Y.

[73] Assignees: Trustees of Boston University, Boston, Mass.; Angio-Medical Corporation, New York, N.Y.

[21] Appl. No.: 805,206

[22] Filed: Dec. 4, 1985

[51] Int. Cl.⁴ .................. A61K 31/70; A61K 31/715; A61K 31/20

[52] U.S. Cl. ........................ 514/25; 514/54; 514/558; 424/95; 424/DIG. 13

[58] Field of Search .......................... 424/95, DIG, 13; 514/25, 54, 558

[56] References Cited

U.S. PATENT DOCUMENTS 4,476,119  10/1984  Dellavalle et al. .................. 514/25

Primary Examiner—John Rollins
Attorney, Agent, or Firm—Felfe & Lynch

[57] ABSTRACT

Omental lipid fractions accelerate wound healing especially as to epithelialization in mammals.

13 Claims, 6 Drawing Sheets

Fig. 1.

Fractionation of Omentum Lipid Extract

Fig. 3A.

Day 3

Fig. 3B.

Day 7

Fig. 3C.

Day 10

Fig. 3D.

Day 14

Fig. 3E.

Day 18

Fig. 3F.

Day 21

Day 24

Day 28

Fig. 3I.

Day 31

Fig. 4.

METHOD FOR ENHANCEMENT OF HEALING OF EPITHELIAL WOUNDS IN MAMMALS

This invention relates to epithelial wound healing in mammals using omental angiogenic factor lipid fractions.

BACKGROUND

We note the U.S. Pat. No. 4,456,596 issued June 26, 1984 to Rolf Schäfer for wound healing compositions consisting of glycosphingolipid, a glycosteroid and a polypeptide. Schäfer uses topical application of the composition. The glycosphingolipid of this patent supposedly promotes middle and end phase healing promoting proliferation of fibroblasts and epithelial cells when used topically on skin ulcers to show enhanced healing after about 6-10 weeks. We note the Schäfer material appears to work only after vascularization and capillarization have begun (See claim 9 therein).

Other patents relate to use of natural materials for wound healing such as fibrinogen from plasma (U.S. Pat. Nos. 4,427,650 issued Jan. 24, 1984 and 4,442,655 issued Apr. 17, 1984 both to Stroetmann), collagen fibers for medical use (U.S. Pat. Nos. 4,420,339 issued Dec. 13, 1983 to Kato, 4,233,360 issued Nov. 11, 1980 to Luck et al. and 3,949,073 to Daniels et al. issued Apr. 6, 1976), glycoprotein from saliva for ulcer treatment (U.S. Pat. No. 3,522,229 issued July 28, 1970 to Yamamoto et al.), sulfonated glycopeptide as anti-inflammatory agents (U.S. Pat. No. 3,518,243 issued June 30, 1970 to Butti et al), fern extract for ulcers (U.S. Pat. No. 3,395,223 issued July 30, 1968 to Berger et al) which appears not to be lipid, and low molecular weight proteins from blood (U.S. Pat. No. 3,672,954 issued June 27, 1972 to Grippa).

Healing is also seen with organic compounds, such as phenyl compounds (U.S. Pat. No. 4,333,940 to Shepard) and acid anhydrides (U.S. Pat. Nos. 2,788,308 issued Apr. 9, 1967 and 3,341,410 issued Sept. 12, 1967 to Ochs). Other aromatic compounds are piperidine and pyridine derivatives (U.S. Pat. Nos. 3,321,484 issued to Krimml May 23, 1967, 3,318,901 issued to Cusic et al. May 9, 1967 U.S. Pat. No. 4,282,250 issued Aug. 4, 1981 to Papageorgiou), anti-inflammatory indole-acetic acid esters (U.S. Pat. No. 3,271,394 issued Sept. 6, 1966 to Shen et al.), cytochrome compositions for ulcerous wounds (U.S. Pat. No. 3,017,325 issued Jan. 16, 1962 to Vogel) and U.S. Pat. No. 3,809,760 for tissue repair issued May 7, 1974 to Thely. Steroids are known for anti-inflammatory action (see U.S. Pat. Nos. 3,047,470 issued July 31, 1962 to Pruess et al 3,767,683 issued Oct. 23, 1973 to Cusic and 2,845,381 issued July 29, 1958 to Tindall), flavylium aromatic salts (U.S. Pat. No. 4,376,781 issued Mar. 15, 1983 to Lietti).

Animal wounds are reportedly healed with long chain polyunsaturated acids of fish oil and terpines plus oleic acid and kerosene mainly to protect wounds (U.S. Pat. No. 4,447,418 issued May 8, 1984 to Maddoux) as is the poly-caprolactone of Gregory (U.S. Pat. No. 4,186,190 issued Jan. 29, 1980) and note U.S. Pat. No. 3,920,848 to Jelenko.

Vitamins A and D, olive oil and an aromatic hydroxyl derivative are used in a lotion (U.S. Pat. No. 3,622,668 issued Nov. 23, 1971 to Moss). Internal use of compositions including prostagladins to treat blood clots is seen in U.S. Pat. No. 4,211,782 issued July 8, 1980 to Vane. A Mollusc extract as protectant is used together with an active drug to treat ulcers (U.S. Pat. No. 4,455,298 issued June 19, 1984 to McFallane) and there is a mixture for ulcer treatment comprising sucrose, glucose, amino acids and lipids as a food (U.S. Pat. No. 4,029,773 issued June 14, 1977 to Beigler et al.).

SUMMARY

This invention concerns healing of epithelial wounds in mammals with omental lipid fractions.

BRIEF DESCRIPTION OF THE DRAWING

FIG. 3 (A-I) shows the wound healing of a control dog starting with day 3 after the initial wound was made.

DESCRIPTION

There is no art dealing with use of omentum, omental fractions or omental lipid fractions in epithelial wound healing. The material of the invention is thus novel as to epithelial wound healing, epithelialization.

Angiogenesis and chemical factors that mediate or inhibit the angiogenic process have important implications in major diseases (Auerbach, R. (1981) in Lymphokines ed E. Pick, Academic Press, Vol. 4., P. 69). Angiogenic factors have been purified from various pathological sources (Schor, A. M. et al. (1983) Tumor Angiogenesis J. Pathology 141:385) and from normal tissue in small quantities (D'Amore, P. A. et al. (1981) Proc. Nat'l Acad. Sci. 78:3068-3072; Frederick, J. L. et al. (1984) Science 224:389-390; Burgos, H. (1983) J. Clin. Invest. 13:289-296). Normal tissue, available in large quantities, that contains potent angiogenic activity provides opportunities for isolation, structural analysis and extensive animal and clinical studies. A chloroform-methanol extract from feline omentum has been previously reported (Goldsmith, H. et al. JAMA 252:15 P.2034) (hereby incorporated by reference) to produce excellent angiogenic activity after a single injection into the central cornea of rabbits. Also see copending U.S. patent application Ser. No. 642,624 filed Aug. 20, 1984, now U.S. Pat. No. 4,699,788 issued Oct. 13, 1987, hereby incorporated by reference. The components of this extract have now been fractionated and the major glycosphinogolipid components characterized. The angiogenic activities, as measured by the chick chorioallantoic membrane (CAM) assay (Folkman, J. (1974) Cancer Res. 34:2109), of the fractions and purified glycosphingolipids have also been determined. Neutral glycosphingolipids and particularly gangliosides have recently been reported to be associated with a variety of cellular responses and have been shown to modulate activity of receptors of several growth factors (Bremer, E. G., et al. (1984) J. Cell. Biol. 259:6818). Our studies indicate that exogenesis glycolipids can influence the angiogenesis response in the chicken egg chorioallantoic membrane system. This information is found in copending U.S. application Ser. No. 782,724 filed Oct. 1, 1985, now U.S. Pat. No. 4,710,496, issued Dec. 1, 1978.

Materials

HPLC grade methanol and other reagent grade solvents and chemicals were obtained from Fisher Chemical Scientific (Fairlawn, NJ); Iatrobeads 6RS-8060 and 6RS-8010 were from Iatron Industries (Tokyo, Japan); DEAE-Sephadex (A-25) was from Pharmacia Fine Chemicals (Piscataway, NJ); Unisil was from Clarkson Chemical Company (Williamsport, PA); and HPTLC plates were obtained from E. Merck (Darmstadt, Germany). Ganglioside and glycolipid standards were prepared as previously described (Velman, M. D., et al. (1977) J. Lipid. Res. 18:371-378; Ledeen, R. W., et al. (1978) in Research Methods in Neurochemistry Vol. 4 ed. Marks and R. Rodnight Plenum Publishing Corp., N.Y. P. 371-410). V. cholerae neuraminidase was obtained from Sigma Chemical Co. (St. Louis, MO).

Methods

Fractionation of Omentum Extracts-Omentum from adult female cats were excised and minced as previously reported (Goldsmith, et al. Supra). The omentum preparations were homogenized in cold phosphate-buffered saline (PBS) and centrifuged at 4° C. for 20 min in 250 ml plastic bottles at 1,600 g. After centrifugation, the lipid cake was removed and homogenized in 20 volumes of chloroform-methanol (2:1). The extract was centrifuged at 200 g for 10 min to remove particulate matter and the clear supernatant was evaporated to dryness/fIin vacuo/fR to obtain the crude lipid extract (CLE) also known as the CMFr.

The CMFr was dissolved in hexane (approximately 60 ml/10 g of extract) and 0.66 volumes of 95% ethanol added (Galanos, D. S. et al. (1962) J. Lipid. Res. 3:134). The phases were thoroughly mixed and allowed to separate. The lower phase was removed and the upper phase (hexane layer) re-extracted with 95% ethanol. The lower phases were combined and re-extracted with a fresh volume of hexane and the hexane phases combined. The phases were then taken to dryness/fIin vacuo/fR to obtain hexane upper phase material (hexane-UP) also known as the HxCMFr and ethanol lower phase material (ethanol-LP) also known as ETCMFr. The hexane phase contained approximately 98% of the material in the CMFr and was shown to consist primarily of triglycerides as determined by Thin Layer Chromatography (TLC). Alkaline hydrolysis and GC/MS analysis of the resulting fatty acid methyl esters revealed that 14:0, 16:0, 16:1, 17:0, 18:0, 18:1 and 18:2 were the major triglyceride fatty acids.

Other hydrocarbons (e.g., pentane, cyclohexane, cyclopentane, benzene, etc.) can be used instead of hexane for the above separation. Methanol., n-propanol, and acetonitrile can be used instead of ethanol for the above separation. Other methods can also be used as seen and obvious to those skilled in the art in Kates, M. (1972) "Techniques of Lipidology: Isolation, Analysis, and Identification of Lipids", (North-Holland Elsevier P. 269-610) hereby incorporated by reference. These methods among others may include acetone precipitation, solvent partition using countercurrent distribution, column chromatography, and/or high pressure liquid chromatography.

Next a Folch partition (Folch, J., et al. (1957) J. Biol. Chem. 226:497-509) was performed. The ethanol-LP was dissolved in chloroform/methanol (2:1) (20 volumes, v/wt) and 0.2 volumes of water added and phases thoroughly mixed and allowed to separate. The upper phase was removed and the lower phase washed with 0.4 volumes of methanol/water (1:1). The upper phases were combined and both phases taken to dryness in vacuo to obtain Folch-UP and Folch-LP material.

Folch-LP material was dissolved in chloroform and subjected to chromatography on a silicic acid (Unisil) column (Vance, D. E., et al. (1967) J. Lipid. Res. 8:621). The Unisil column was eluted successively with 20 column volumes of chloroform, acetone/methanol (9:1), and methanol to obtain the neutral lipid, glycolipid and phospholipid fractions, respectively. The neutral lipid fraction consisted primarily of triglycerides and small amounts of cholesterol and free fatty acids as detected by TLC analysis. The acetone glycolipid fraction was examined by TLC and components migrating as hexosylceramide, lactosylceramide, globotriaosylceramide and globoside were present. HPLC analysis of the lower phase glycolipids showed Glc Cer (Nfa), 26%; Gal Cer (N fa), 9.6%; Glc Cer (H fa)+Gal Cer (H fa)+GaOse 2 Cer (N fa), 12%; lac Cer, 11%, GbOse Cer, 10% GbOse4Cer, 26%. The methanol phospholipid fraction was examined by TLC and components migrating as phosphatidylserine, phosphatidylcholine and sphingomyelin were present.

The Folch-UP material was dissolved in methanol/water (1:1) (approximately 20% by weight of the Ethanol-phase material) (approximately 3 ml/mg) and applied to a C18 reversed-phase cartridge (BondElut) (Williams, M. et al. (1980) J. Neurochem. 35:266-269) which was then washed with 4 volumes of methanol/water (1:1) followed by elution with 4 volumes of chloroform/methanol (2:1). The two washes were separately collected and evaporated to dryness/fIin vacuo/fR to obtain non-lipid material (non-lipid-UP) and lipid material (lipid-UP) respectively.

Figure 1:
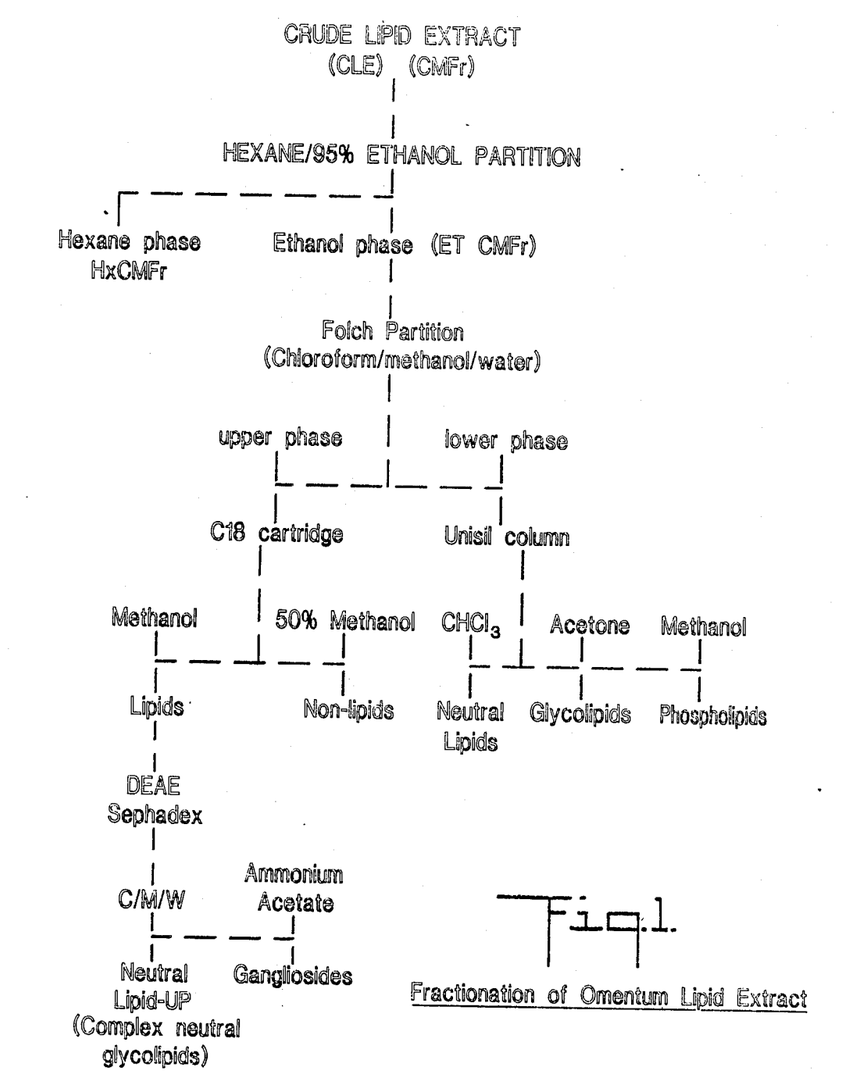
FIG. 1 shows the method of isolation of omental lipid fractions.

The lipid-UP material was dissolved in methanol/chloroform/water (60:30:8) and applied to a DEAE-Sephadex [acetate] column (Christie, W. W. (1982) Lipid Analysis, Pergamon Press 2nd Ed. P. 109-110). The column was eluted with 10 volumes of the same solvent to obtain the neutral lipid upper phase fraction (neutral lipid-UP) consisting of a glycolipid migrating below globoside) and small amounts of more complex glycolipids. The column was then eluted with methanol/chloroform/0.8M sodium acetate (60:30:8) to obtain the ganglioside fraction. The fractions were evaporated to dryness /fIin vacuo/fR. The ganglioside fraction was desalted with a C18 reversed-phase cartridge as described above. HPTLC showed the presence of $GM_3$, $GM_1$, $GD_3$ and several minor polysialogangliosides (GD1a and GT1b). The $GD_3$ ratio of Glc/Gal was 1:1 and the major fatty acid components were 16:01, 18:0, 18:1, 24:0 and 24:1. Neuraminadase treatment produced lactosylceramide. The liberated sialic acid was N-acetylneuraminic. A flow chart of the fractionation scheme is shown below (FIG. 1).

Omenta were extracted from feline and bovine sources as previously described Goldsmith et al. (1984) J. Amer. Med. Assn. 252:15, pp. 2034-2036 to yield a chloroform methanol extract (CME) also known as the CMFr. This CMFr is further extracted with hexane to yield a neutral lipid fraction from the CMFr known as the HxCMFr. Other lipid extraction methods can be used as well. The invention is not limited by the extraction method described above which is for illustrative purposes. Bovine, ovine and porcine omenta can also be extracted in the like manner.

It is also possible to extract omentum using other organic solvents to obtain active angiogenic fractions. We also note the use of supercritical gas extraction for extraction of omentum factors as described in our co-pending application Ser. No. 793,645 filed Oct. 31, 1985, now U.S. Pat. No. 4,673,667 issued June 16, 1987 and hereby incorporated by reference.

Supercritical gas extraction is also used to extract omental materials as in the co-pending U.S. application Ser. No. 793,622 filed Oct. 31, 1985 by Kamarei. Here a supercritical fluid (SCF) $CO_2$ is used to extract omentum. An SCF has increased solvation power at temperatures above the critical pressure ($P_c$) and critical temperature ($T_c$).

$Co_2$ is used. Polar materials such as gangliosides remain in the residue while the extract contains the more non-polar or lipid materials such as triglycerides. Temperatures used are 38–39° C. and pressures are 3500 psig. Thus these conditions can avoid extraction with toxic materials, or inefficient extraction or use of expensive and time-consuming extractions and materials.

Use of Detergents for Lipid Isolation

Lipids are displaced from homogenized cell membranes, or other complexes involving proteins, by amphipathic detergent molecules which render the proteins "soluble" in aqueous media. The released lipid material is recovered by flotation after centrifugation.

A list of possible detergents is given in tables A and B. These are used in concentrations ranging from 0.1 to 2.0% (w/v) and a pH from 7.0 to 8.0.

Cryogenic Methods

Omenta can be extracted as above after subdivision in liquid nitrogen.

TABLE A

| | DETERGENTS WITH FLEXIBLE HYDROPHOBIC REGIONS | |
|---|---|---|
| Detergent type | Structural formula | Formal (and trivial) name |
| Strongly ionic |  | Sodium dodecylsulphate |
| |  | Cetyltrimethylammonium bromide |
| "Weakly" ionic |  | Sodium dodecyl—N—sarcosinate (sarkosyl) |
| Zwitterionic |  | Sulfobetaine (Zwittergent)[a] |
| |  | Palmitoyllysolecithin |
| "Weakly" Zwitterionic |  | Dimethylalkylamine oxides (Ammonyx LO)[b] |
| Non-ionic |  | Polyoxyethylene alcohol (Brij series, Lubrol W.AL.P series) |
| |  | Polyoxyethylene nonylphenol (Triton N series Igepal CO series Surfonic N series Emulgen series) |
| Non-ionic with branched hydrophobic region |  | Polyoxyethylene p.t.octyl phenol (Triton X series Igepal CA series Nonide: P40) |

[a]Available from Calbiochem-Behring, Serva.
[b]Available from Onyx Chemical Co., 190 Warren Street, Jersey City, NJ 07032 U.S.A.

TABLE B
DETERGENTS WITH RIGID HYDROPHOBIC REGIONS

| Detergent type | Structural formula | Formal (and trivial) name |
|---|---|---|
| Strongly ionic | [steroid structure with OH, HO, OH, COO⁻Na⁺] | Sodium cholate |
| 'Weakly' ionic | [steroid structure with C(=O)—NH—CH₂—CH₂—S(=O)₂—O⁻Na⁺] | Sodium taurocholate |
| Zwitterionic | [steroid structure with —C(=O)—N—(CH₂)₃—N⁺—(CH₂)₃—S(=O)₂—O⁻] | CHAPS[a] |
| Non-ionic | [steroid structure with sugars: 2 Galactose, 2 Glucose, 1 Xylose] | Digitonin |

[a] 3-[(3-cholamidopropyl) dimethylammonio]-1-propanesulphonate, available from Calbiochem-Behring, Serva.

Drawings

FIG. 1 is a flow chart of the fractionation scheme for cat omenta.

Figure 2:
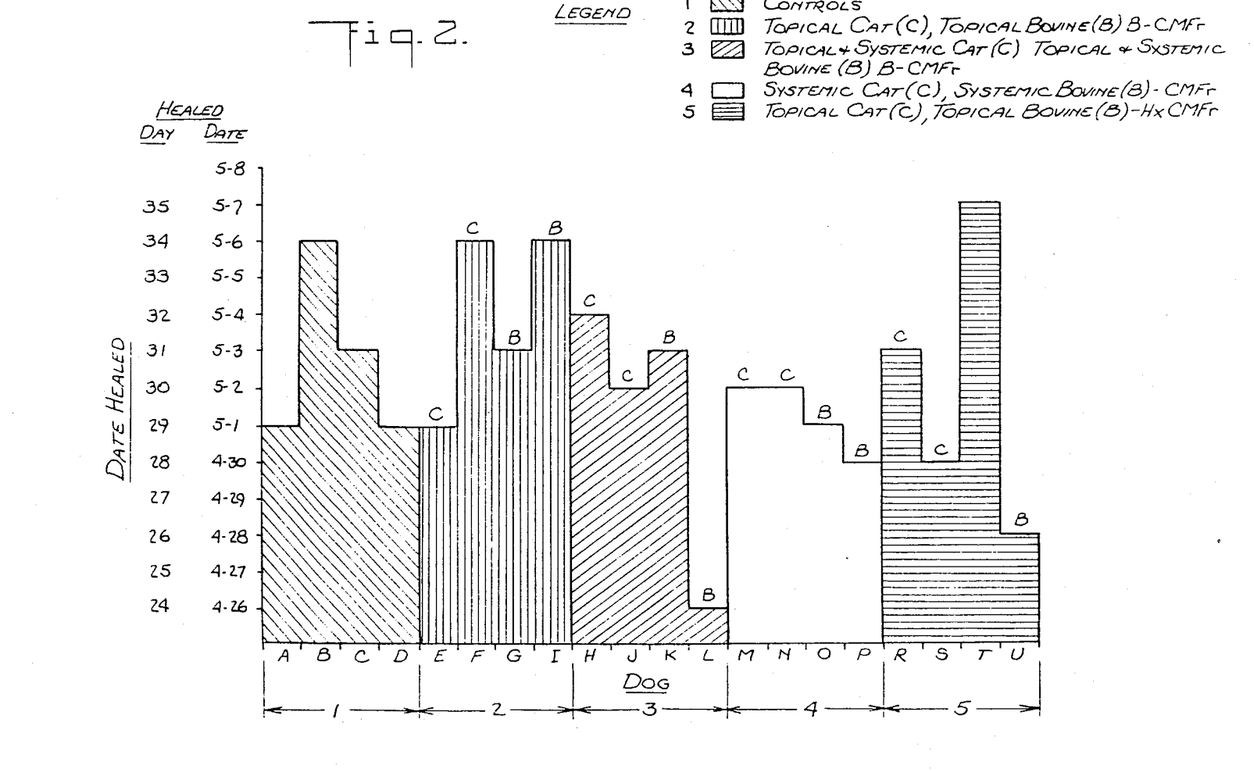
FIG. 2 shows epithelial wound healing in experimental and control dogs.
Figure 3A:
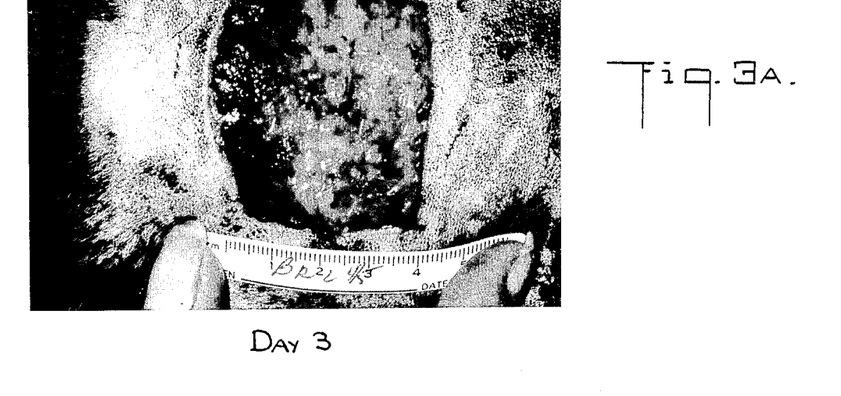
Figure 3B:
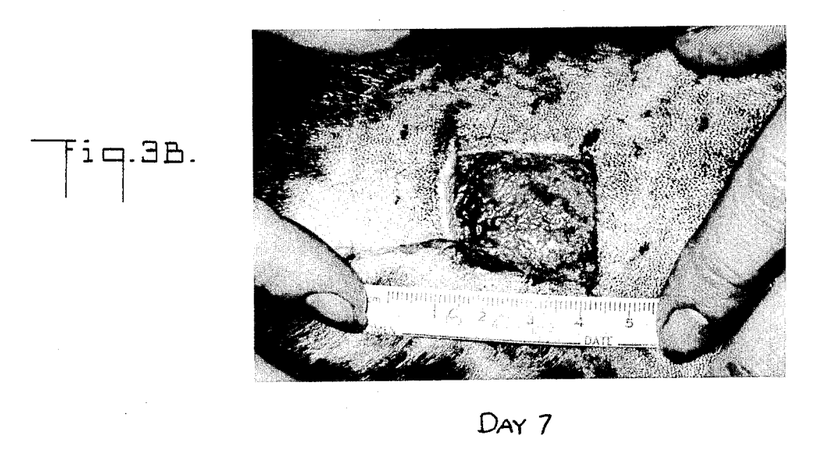
Figure 3C:
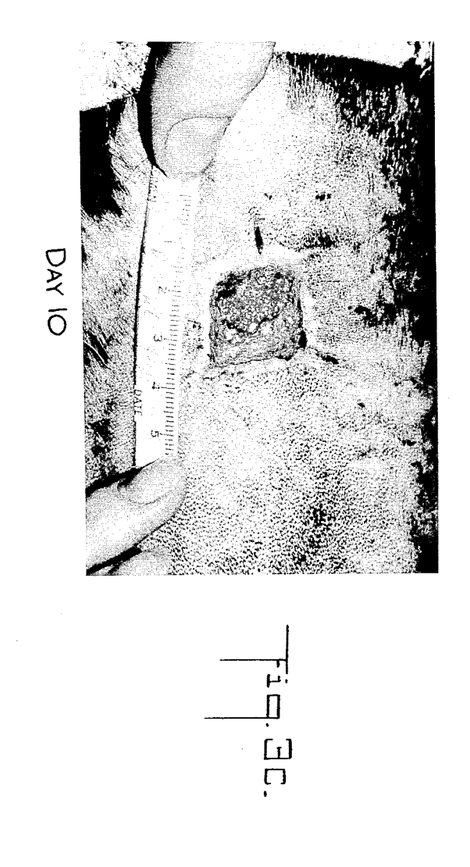
Figure 3D:
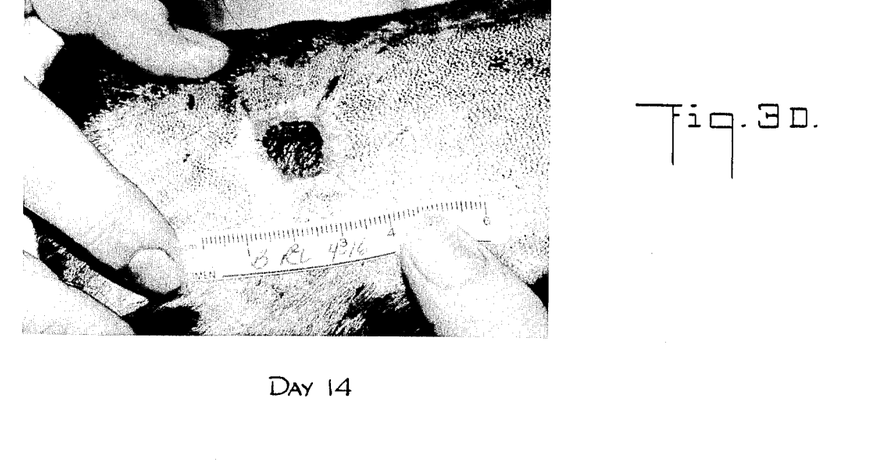
Figure 3E:
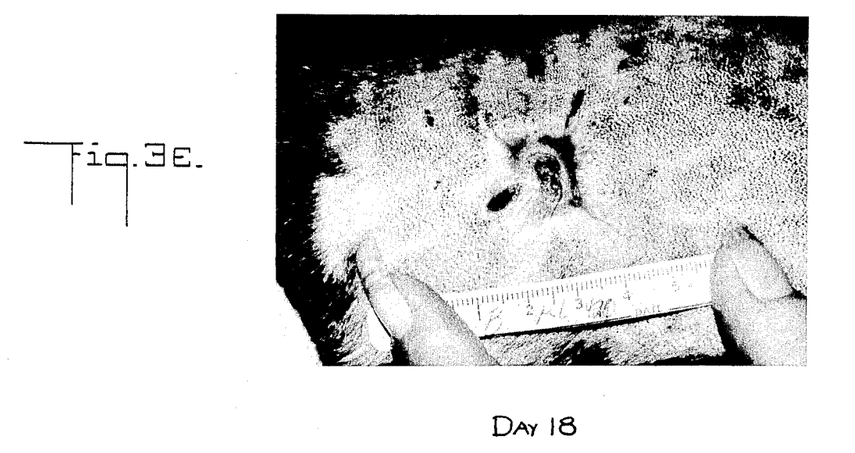
Figure 3F:
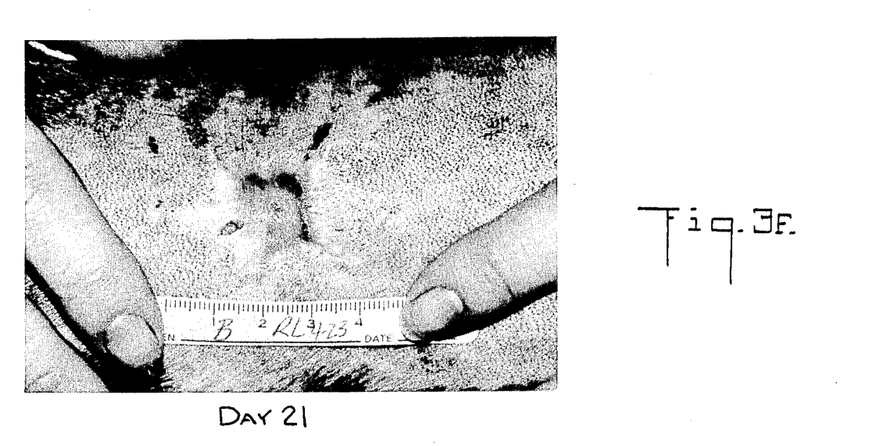
Figure 3G:
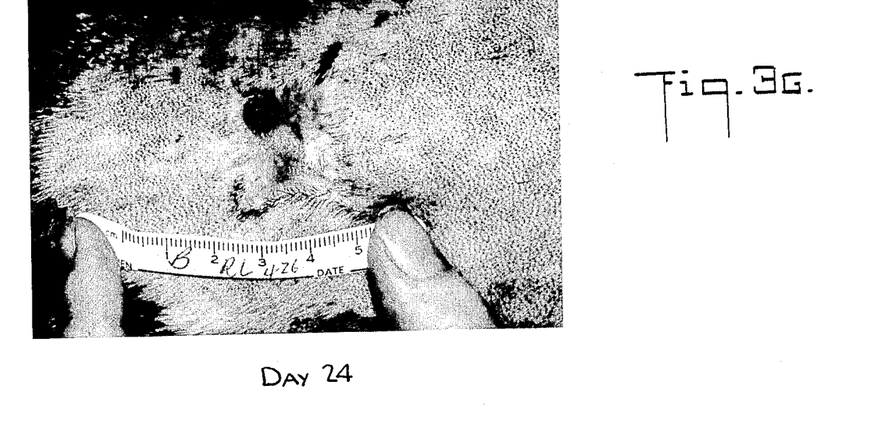
Figure 3H:
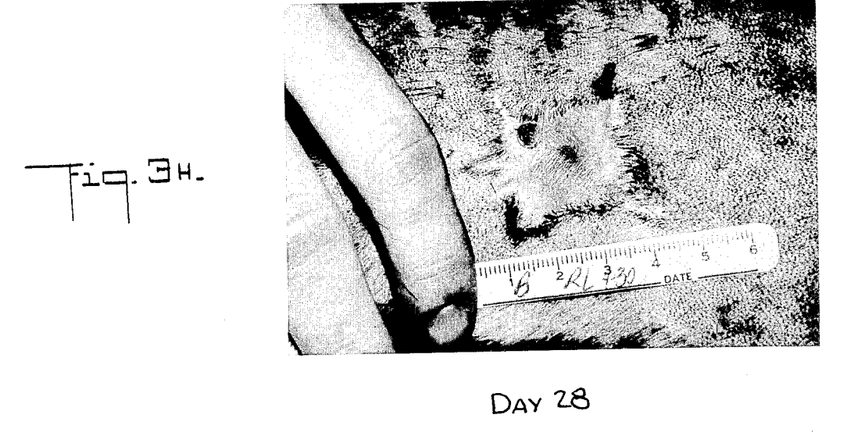
Figure 3I:
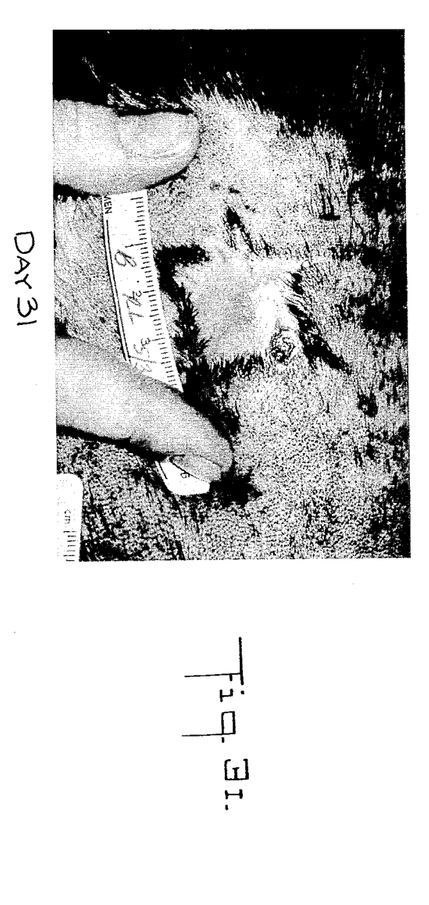

FIG. 2 shows wound closing dates for open wounds for specific control (1) and experimental dogs (2-5).

FIG. 3 (A-I) shows wound healing over a period of time for a wound on a control dog.

Figure 4:
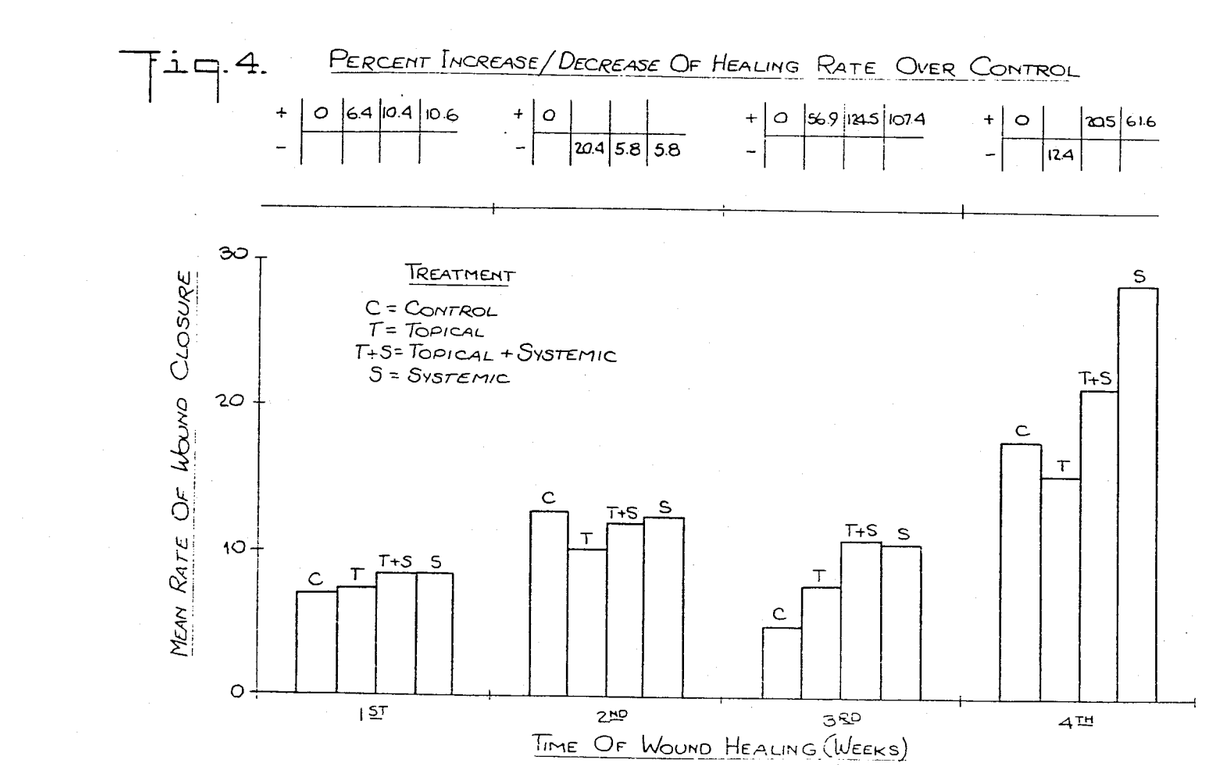
FIG. 4 shows mean wound healing closure rate as the slope produced by linear regression of the log (wound area) as a function of time (in weeks).

FIG. 4 shows mean rates of wound closure as slope produced by linear regression of the log (wound area) plotted against time (in weeks).

The examples below are for illustrative purposes and the invention is not limited thereby.

EXAMPLE I

Epithelial Wound Healing

Full thickness skin wounds, including the underlying cutaneous muscles, were made over the thoracic, abdominal and lumbar areas in 20 adult female beagle dogs by Dr. Dudley Johnston at the University of Pennsylvania School of Veterinary Medicine, Philadelphia, Pa. Each dog had 6 wounds, 3 on each side of the dorsal mid-line, each wound measured 4 cm×4 cm. Wounds were in similar positions in each dog. All 20 dogs were the same age, sex and breed and ranged in weight from 6.4 kg to 8.2 kg. All dogs were fully conditioned experimental dogs in excellent health. For the initial surgical procedure, subsequent wound measurements and biopsies, dogs were sedated with oxymorphone 100 microgram/kg IM and atropine 0.02 mg/kg I.M. Brief anesthesia was induced with thiopentone 2 mg/kg IV and continued to effect.

Each wound was outlined by a square tattoo prior to wound incision. The tattoo marks bordered the excised zone and the marks served to indicate the original edge of the wound in photographs. Open wounds after surgery or medication were covered by a vaseline gauze non-adherent dressing, absorbent cotton and a body bandage. The two central (abdominal) wounds in all dogs were immediately grafted with full thickness skin obtained from the adjacent lumbar wound. Each graft was sutured in place with 8 simple interrupted sutures.

Each wound was photographed after surgery using a fixed lens-wound distance. Wound distance and the area of the wound was determined from photographs, as described below. Wound healing for each group was evaluated quantitatively as described below on days 3, 7, 10, 14, 18, 21, 28 and 31.

The twenty dogs were divided into five groups of four dogs as seen in FIG. 2.

In the 4 control dogs (Group 1:dogs A, B, C D), wounds were treated every 8 hours with warm isotonic saline to remove crusts, discharges etc. Wound dressings were re-applied every third treatment (once daily).

In 4 experimental dogs (Group 2:dogs E, F, G and I) there was topical application of either bovine or feline CMFr (0.3 g). At the end of the surgical protocol, chloroform-methanol extract (CMFr) from cat or bovine extract was applied to the wound surface and this was covered by vaseline gauze. CMFr was also applied to the autografted skin. Wounds were cleaned every 8 hours as for control wounds. CMFr was re-applied beneath vaseline gauze dressings every 8 hours to open wounds only (not grafts)

In another 4 experimental dogs (Groups 3:dogs H, J, K and L) there was topical plus systemic application of the feline or bovine CMFr. Topical application was done as above. In addition these dogs received daily I.M. injections of feline or bovine CMFr - 0.5 ml/Kg body weight. The lipid material was warmed to 37° C. immediately prior to administration to lower the viscosity and to allow injection with a syringe and 19 gauge needle. Dogs in this group were treated both topically and systemically with either bovine or feline CMFr.

In another 4 experimental dogs (Group 4:dogs M,N,O,P) there was systemic application of the CMFr. Dogs M,N,O and P received daily I.M. injections of CMFr, 0.5 ml/Kg body weight. Wounds were treated as for control wounds.

In another 4 experimental dogs (Group 5:dogs R,S,T,U) there was topical application of the HxCMFr. This was done as for the topical application above, except the predominantly triglyceride containing fraction of bovine or feline HxCMFr was applied to the wounds.

Each open wound was assessed every 24 hours for general appearance and was photographed every 3 or 4 days to assess overall size (degree of contraction and size of epithelialized area). Wounds were photographed on days 3,7,10,14,18,21,24,28, and 31. The film - subject distance was identical for all photographs and, as an additional check for uniform size of image, a metric measuring device was attached to normal skin adjacent to the wound margin and included in the photographic image. Photographs were used later to calculate (1) the total wound size and (2) the size of the non-ethelialized area. To calculate wound areas, the photographic images were enlarged by means of a LEITZ VALOY II enlarger with a 50 mm NIKON 1:2.8 MM LENS. The photographic images were enlarged so that one cm on the slide scale was equal to 3.5 cms. Each photographic image was traced on white paper to give a drawing of the total wound area (outer wound) and a drawing of the non-epithelialized area (inner wounds).

The surface areas of the outer wounds and the inner wounds were calculated by computer analysis, using an Apple II E computer, a Houston Instrument HIPAD DIGITIZER and a semi-automatic image analyzer (OPTOMAX INC., 9 Ash Street, Rt. 130, Hollis, N.H. 03049). A correction factor for image magnification was included in the computer programming. Wound areas were statistically analyzed by analysis of variance and covariance with repeated measures (BMPD Statistical Software, Inc. 1964 Westwood Blvd., Suite 202, University of California, Los Angeles, Calif.

A punch biopsy was obtained from each wound margin for histological evaluation of angiogenesis and skin viability days 7,14,21 and 28. Biopsies inlcuded adjacent skin, wound margin and epithelialized wound. Biopsies were examined by one pathologist who was informed of date of biopsy but not treatment group. Biopsies were examined quantitatively for degree of angiogenesis and qualitatively for maturity of healing.

EXAMPLE I

Assessment of Wound Contraction

All dogs tolerated well the surgical procedures and wound dressings and remained healthy throughout the experimental period.

Local tolerance of this product was excellent and no irritation or inflammation was seen. Reaction to the triglyceride fraction is discussed below. In a preliminary pilot trial, CMFr 20% in a standard ointment base was extremely irritating, a finding that must be attributable to the ointment base.

CMFr was difficult to inject locally because of its consistency. Injection with a 19 gauge needle was possible only after warming. CMFr of bovine origin had a thicker consistency than the CMFr of cat origin and was poorly absorbed after I.M. injection. Material injected 24 hours previously was oozing from skin openings and could be palpated in the tissues. This problem was not seen with CMFr of cat origin. No local infection or abscessation was seen after I.M. injection.

1. Open Wounds

All wounds increased in size immediately after surgery and the original square shape was deformed by muscle contraction. A distinct line of regenerating epithelum was seen at 7 days in all wounds, with no discernible difference between groups. Wounds receiving triglycerides had a wound discharge which was more copious, thicker, more yellow and more odoriferous than the discharge from other wounds.

Inner Wounds

The inner wound area represented the area of the wound remaining after contraction and epithelialization. Inner wound areas were evaluated statistically by comparing the square roots of the areas. In each group of 4 dogs, there were 16 wounds, divided into 4 left thoracic, 4 left lumbar, 4 right thoracic and 4 right lumbar. Groups were compared on the basis of total wounds (16) and wounds in each anatomic area (4). Wound area measurements on each of 8 days were available for analysis, a total of 16 wounds in 4 groups on 8 days amounting to 512 wound areas. A summary of all wounds is shown in Table 1. An increase in the rate of healing occurred in left thoracic wounds that were treated systemically with CMFr (Group 4) and in left abdominal wounds in all treatment groups (Tables 2 and 3). It can be seen in Table 4 - analysis of variance for 1st dependent variable (surface area) that differences based on location, side, time and group (LSTG) are significant, $T=0.019$ and differences based on side and group (SG) could be significant, $T=0.1611$. Differences between group based on location, not side, were less likely to be significant. This is emphasized in Tables 2 and 3.

Outer Wounds

A similar number of wounds and groups were evaluated by comparing the outer wound area. This area represents the size of the wound after wound contraction only. No treatment group produced significant increase in wound closure rates, however, the difference between groups based on side time and group (ST6) was probably significant (T=0.0785) (Table 5 and 6).

The linear rate of movement of wound margins were determined by equation in order to obtain a parameter for quantitative comparison of rates of contraction. Wound areas are determined by orthoflex digital coordinate sensor coupled to a programmable printing calculator (Snowden, John M. (1981): Wound contraction. A quantitative interpretation. AJEBAM 59:203).

The periphery of each wound was observed as it healed. As each 4×4 cm wound healed and became smaller, i.e. the edges moving inwards towards the center, there was an area of new epithelium formed (E). The computer measured the area of wound showing decrease thereby measuring the end result of wound healing i.e. how fast the scar had formed.

Neovascularization was assessed histologically, both qualitatively and quantitatively. The quantitative measurement depended on the use of special stains for endothelium and counting numbers and size of vessels.

In FIG. 2 are shown results of the experiments in which the cat (C) and bovine (B) CMFr and HxCMFr were applied both topically and systemically to the wounds. Area 1 represents the control dogs. Area 2 represents those wounds on dogs treated topically with cat and bovine CMFr. Area 3 represents those dog wounds treated both topically and systemically with cat and bovine CMFr. Area 4 represents those dog wounds treated systemically with bovine and cat CMFr. Area 5 represents those wounds treated topically with cat and bovine neutral omental lipids HxCMFr. Each vertical bar represents the time for wounds to heal on each dog i.e. A, B, C, D etc. are individual dogs. FIG. 3 (A-I) shows sequential healing of such a control wound.

Previous experiments done with wound healing in this manner show irritation of the wounds with a CMFr extract in an ointment base applied topically. This delayed wound healing. The ointment base was Aquaphor ® from Beirsdorf Inc. Norwalk, Conn. and contained petrolatum, mineral oil, mineral wax (ceresin wax), and wool wax oil (lanolin, alcohol, and cholesterol). Wounds receiving pure CMFr as above healed well with no irritation and epithelialization was more rapid and complete than in the control dogs.

The unusual and unexpected healing properties and non-irritation of the wound by the CMFr (or CMFr hexane fraction is therefore novel and unexpected especially since it has a creme like appearance.

We note some accelerated healing in treated dogs. The CMFr treated dogs generally did not show the extended time of healing found in the controls of up to 34 days. In general the CMFr reduced the number of slow healers in the groups. This effect is also shown for the systemic experiment (area 4 of the graph). In general the controls healed on the average in 31 days, area 3 and 4 in 29 days and area 2 (topical only) in 32 days. FIG. 3 (A-I) shows photographs of the progressive healing of a control dog (B) wound for days 3, 7, 10, 14, 18, 21, 24, 28 and 31.

Therefore the systemic group (3 and 4) showed a 2 day faster healing rate, 6.4% faster rate than the controls.

TABLE 1

MEANS OF SQUARE ROOT OF INNER WOUND AREA FOR FOUR DOGS OF EACH OF GROUPS 1-4*

| | GROUP = | | Group 1 CONTROL | Group 2 TOPICAL | Group 3 TOPICAL & SYSTEMIC | Group 4 SYSTEMIC | Group 5 MARGINAL OVERALL |
|---|---|---|---|---|---|---|---|
| | LOC | SIDE | TIME | (N = 4) | (N = 4) | (N = 4) | (N = 4) | (N = 16) |
| LEFT THORACIC | 1 | 1 | 3 | 35.52499 | 29.59999 | 34.57499 | 34.97499 | 33.66874 |
| | 1 | 1 | 7 | 26.17500 | 20.52500 | 23.30000 | 24.75000 | 23.68750 |
| | 1 | 1 | 10 | 16.80000 | 14.44999 | 12.72500 | 15.57500 | 14.88750 |
| | 1 | 1 | 14 | 9.92500 | 10.72500 | 8.00000 | 9.40000 | 9.51250 |
| | 1 | 1 | 18 | 9.40000 | 8.30000 | 4.10000 | 7.85000 | 7.41250 |
| | 1 | 1 | 21 | 6.87500 | 6.52500 | 5.82500 | 4.87500 | 9.52500 |
| | 1 | 1 | 24 | 4.27500 | 3.47500 | 2.82500 | 1.62500 | 3.05000 |
| | 1 | 1 | 28 | 2.47500 | 1.15000 | 2.15000 | 0.00000 | 1.44375 |
| RIGHT THORACIC | 1 | 2 | 3 | 34.57499 | 37.19999 | 34.64999 | 31.25000 | 34.41874 |
| | 1 | 2 | 7 | 24.57500 | 24.87499 | 25.14999 | 21.79999 | 24.09999 |
| | 1 | 2 | 10 | 15.05000 | 15.17500 | 13.62500 | 13.42500 | 14.31875 |
| | 1 | 2 | 14 | 6.65000 | 10.15000 | 9.47500 | 7.52500 | 8.45000 |
| | 1 | 2 | 18 | 6.37500 | 7.35000 | 6.95000 | 4.60000 | 6.31875 |
| | 1 | 2 | 21 | 6.77500 | 6.57500 | 3.55000 | 2.97500 | 4.96875 |
| | 1 | 2 | 24 | 4.90000 | 4.00000 | 2.67500 | 1.77500 | 3.33750 |
| | 1 | 2 | 28 | 0.00000 | 3.20000 | 1.27500 | 1.65000 | 1.53125 |
| LEFT LUMBAR | 2 | 1 | 3 | 33.32499 | 32.25000 | 34.49999 | 31.97499 | 33.01249 |
| | 2 | 1 | 7 | 24.44999 | 23.97499 | 23.17500 | 21.89999 | 23.37499 |
| | 2 | 1 | 10 | 14.72500 | 15.24999 | 14.45000 | 15.67500 | 15.02500 |
| | 2 | 1 | 14 | 9.67500 | 9.07500 | 7.92500 | 9.15000 | 8.95625 |
| | 2 | 1 | 18 | 7.97500 | 6.40000 | 4.25000 | 6.50000 | 6.28125 |
| | 2 | 1 | 21 | 6.52500 | 3.22500 | 2.42500 | 4.60000 | 4.19375 |
| | 2 | 1 | 24 | 4.90000 | 1.00000 | 0.90000 | 1.20000 | 2.00000 |
| | 2 | 1 | 28 | 2.92500 | 0.00000 | 0.60000 | 0.00000 | 0.88125 |
| RIGHT LUMBAR | 2 | 2 | 3 | 31.49999 | 34.22499 | 31.22499 | 23.92500 | 30.21874 |
| | 2 | 2 | 7 | 22.22499 | 25.32499 | 19.00000 | 21.77499 | 22.08124 |
| | 2 | 2 | 10 | 13.32500 | 16.42500 | 14.49999 | 14.47500 | 14.68125 |
| | 2 | 2 | 14 | 9.20000 | 11.20000 | 8.65000 | 7.25000 | 9.07500 |
| | 2 | 2 | 18 | 5.67500 | 7.57500 | 3.95000 | 5.70000 | 5.72500 |
| | 2 | 2 | 21 | 5.75000 | 6.90000 | 3.20000 | 2.07500 | 4.48125 |
| | 2 | 2 | 24 | 1.50000 | 2.90000 | 0.70000 | 0.42500 | 1.38125 |
| | 2 | 2 | 28 | 0.00000 | 1.80000 | 0.00000 | 0.00000 | 0.45000 |
| | | MARGINAL COUNT | | 12.62578 | 12.52500 | 11.25937 | 11.39609 | 11.95156 |

TABLE 1-continued

MEANS OF SQUARE ROOT OF INNER WOUND AREA FOR FOUR DOGS OF EACH OF GROUPS 1-4*

| GROUP = LOC SIDE TIME | Group 1 CONTROL (N = 4) | Group 2 TOPICAL (N = 4) | Group 3 TOPICAL & SYSTEMIC (N = 4) | Group 4 SYSTEMIC (N = 4) | Group 5 MARGINAL OVERALL (N = 16) |
|---|---|---|---|---|---|
| | 4 | 4 | 4 | 4 | 16 |

*group 1-4 as seen in FIG. 2.

TABLE 2

HEALING OF LEFT THORACIC WOUNDS

| Day | Group 1 Control | Group 4 Systemic |
|---|---|---|
| 3 | 35.5 | 35.0 |
| 7 | 26.2 | 24.8 |
| 10 | 16.8 | 15.6 |
| 14 | 9.9 | 9.4 |
| 18 | 9.4 | 7.9 |
| 21 | 6.9 | 4.9 |
| 24 | 4.3 | 1.6 |
| 28 | 2.5 | 0.0 |

Square roots of surface area of non-epithelialized zone.

TABLE 3

HEALING OF LEFT ABDOMINAL WOUNDS

| Day | Group 1 Control | Group 2 Topical | Group 3 Topical & Systemic | Group 4 Systemic |
|---|---|---|---|---|
| 3 | 33.3 | 32.3 | 34.5 | 32.0 |
| 7 | 24.4 | 24.0 | 23.2 | 22.0 |
| 10 | 14.7 | 15.2 | 14.5 | 15.7 |
| 14 | 9.7 | 9.1 | 7.9 | 9.2 |
| 18 | 8.0 | 6.4 | 4.3 | 6.5 |
| 21 | 6.5 | 3.2 | 2.4 | 4.6 |
| 24 | 4.9 | 1.0 | 0.9 | 1.2 |
| 28 | 2.9 | 0.0 | 0.6 | 0.0 |

Square roots of surface area of non-epithelialized zone.

TABLE 4

ANALYSIS OF VARIANCE FOR INNER WOUND AREA

| SOURCE | SUM OF SQUARES | DEGREES OF FREEDOM | MEAN SQUARE | F | TAIL PROB. |
|---|---|---|---|---|---|
| Group | 201.70339 | 3 | 67.23446 | 0.93 | 0.4622 |
| 1-st Covar | 57.02629 | 1 | 57.02629 | 0.79 | 0.3956 |
| 2-nd Covar | 228.06480 | 1 | 228.06480 | 3.15 | 0.1063 |
| All Covariates | 322.58714 | 2 | 161.29357 | 2.23 | 0.1584 |
| 1 Error | 723.89303 | 10 | 72.38930 | | |
| Loc | 68.21324 | 1 | 68.21324 | 2.02 | 0.1853 |
| LG | 28.42555 | 3 | 9.47518 | 0.28 | 0.8379 |
| 1-st Covar | 11.17497 | 1 | 11.17497 | 0.33 | 0.5775 |
| 2-nd Covar | 22.83479 | 1 | 22.83479 | 0.68 | 0.4297 |
| All Covariates | 61.45133 | 2 | 30.72567 | 0.91 | 0.4329 |
| 2 Error | 337.08530 | 10 | 33.70853 | | |
| Side | 8.14117 | 1 | 8.14117 | 0.55 | 0.4758 |
| SG | 94.37138 | 3 | 31.45713 | 2.12 | 0.1611 |
| 1-st Covar | 27.59390 | 1 | 27.59390 | 1.86 | 0.2025 |
| 2-nd Covar | 1.36814 | 1 | 1.36814 | 0.09 | 0.7676 |
| All Covariates | 42.78841 | 2 | 21.39421 | 1.44 | 0.2816 |
| 3 Error | 148.33295 | 10 | 14.83330 | | |
| LS | 2.29020 | 1 | 2.29020 | 0.28 | 0.6091 |
| LSG | 24.72184 | 3 | 8.24061 | 1.00 | 0.4313 |
| 1-st Covar | 29.26487 | 1 | 29.26487 | 3.56 | 0.0885 |
| 2-nd Covar | 11.51393 | 1 | 11.51393 | 1.40 | 0.2639 |
| All Covariates | 35.54671 | 2 | 17.77336 | 2.16 | 0.1658 |
| 4 Error | 82.18935 | 10 | 8.21894 | | |
| Time | 56948.23582 | 7 | 8135.46226 | 887.65 | 0.0000 |
| TG | 127.65651 | 21 | 6.07888 | 0.66 | 0.8565 |
| 5 Error | 769.87792 | 84 | 9.16521 | | |
| LT | 48.32777 | 7 | 6.90397 | 1.40 | 0.2167 |
| LTG | 102.16552 | 21 | 4.86502 | 0.99 | 0.4890 |
| 6 Error | 414.64101 | 84 | 4.93620 | | |
| ST | 6.30827 | 7 | 0.90118 | 0.20 | 0.9852 |
| STG | 132.24720 | 21 | 6.29749 | 1.38 | 0.1525 |
| 7 Error | 383.41908 | 84 | 4.56451 | | |
| LST | 40.09014 | 7 | 5.72716 | 1.77 | 0.1037 |
| LSTG | 130.63380 | 21 | 6.22066 | 1.92 | 0.0191 |
| 8 Error | 271.52935 | 84 | 3.23249 | | |

TABLE 5

OUTER WOUND AREAS IN CONTROL AND TREATED GROUPS

| | GROUP = | | | | | | |
|---|---|---|---|---|---|---|---|
| | LOC | SIDE | TIME | CON | TOP | TS | SYS |
| D1 | 1 | 1 | 1 | 36.81407 | 35.29332 | 35.88993 | 37.11923 |
| D2 | 1 | 1 | 2 | 29.11408 | 26.46832 | 26.68992 | 28.31923 |
| D3 | 1 | 1 | 3 | 22.78908 | 20.96832 | 20.96492 | 23.09423 |
| D4 | 1 | 1 | 4 | 20.58908 | 18.79331 | 18.93992 | 19.94423 |
| D5 | 1 | 1 | 5 | 18.96408 | 17.26831 | 19.43992 | 19.64424 |
| D6 | 1 | 1 | 6 | 17.41408 | 17.41831 | 18.38993 | 17.69423 |
| D7 | 1 | 1 | 7 | 16.53907 | 16.26832 | 16.76493 | 17.06924 |

TABLE 5-continued
OUTER WOUND AREAS IN CONTROL AND TREATED GROUPS

| | GROUP = | | | | | | |
|---|---|---|---|---|---|---|---|
| | LOC | SIDE | TIME | CON | TOP | TS | SYS |
| D8 | 1 | 1 | 8 | 17.06408 | 17.01832 | 16.51493 | 16.89423 |
| D9 | 1 | 2 | 1 | 35.18871 | 35.91726 | 35.30785 | 33.75372 |
| D10 | 1 | 2 | 2 | 28.18871 | 26.74226 | 27.83285 | 26.15372 |
| D11 | 1 | 2 | 3 | 21.73871 | 20.54226 | 22.25785 | 23.10372 |
| D12 | 1 | 2 | 4 | 19.66371 | 18.44227 | 19.23286 | 19.25372 |
| D13 | 1 | 2 | 5 | 18.43871 | 16.81727 | 20.43285 | 20.37872 |
| D14 | 1 | 2 | 6 | 17.78871 | 16.79227 | 18.75785 | 17.47872 |
| D15 | 1 | 2 | 7 | 15.43872 | 17.36727 | 17.83286 | 16.92872 |
| D16 | 1 | 2 | 8 | 16.38871 | 17.01727 | 17.50785 | 16.92872 |
| D17 | 2 | 1 | 1 | 34.37786 | 35.49797 | 36.61790 | 34.73817 |
| D18 | 2 | 1 | 2 | 26.15286 | 29.14796 | 27.71790 | 26.03817 |
| D19 | 2 | 1 | 3 | 22.37786 | 22.99796 | 23.46790 | 25.58817 |
| D20 | 2 | 1 | 4 | 22.35286 | 24.07296 | 22.29290 | 22.11317 |
| D21 | 2 | 1 | 5 | 19.12786 | 21.84796 | 23.09290 | 21.21316 |
| D22 | 2 | 1 | 6 | 19.17786 | 23.09797 | 23.14290 | 20.53816 |
| D23 | 2 | 1 | 7 | 18.77786 | 22.49796 | 21.86790 | 19.81316 |
| D24 | 2 | 1 | 8 | 20.45286 | 22.62297 | 22.76791 | 19.83816 |
| D25 | 2 | 2 | 1 | 33.98525 | 35.06224 | 38.50640 | 33.90504 |
| D26 | 2 | 2 | 2 | 26.06025 | 28.18723 | 28.15640 | 26.00504 |
| D27 | 2 | 2 | 3 | 22.46025 | 23.91223 | 24.55640 | 23.18004 |
| D28 | 2 | 2 | 4 | 23.11025 | 23.13724 | 23.50640 | 22.23004 |
| D29 | 2 | 2 | 5 | 22.58525 | 21.06224 | 24.15640 | 20.68004 |
| D30 | 2 | 2 | 6 | 22.16025 | 21.48723 | 22.90640 | 21.23004 |
| D31 | 2 | 2 | 7 | 22.38525 | 20.51224 | 22.33140 | 20.05504 |
| D32 | 2 | 2 | 8 | 24.03525 | 21.81223 | 22.75640 | 19.65504 |

Number of integer words of storage 8226
used in preceding problem
CPU Time Used 1.335 seconds
Areas expressed as square roots:

Location 1 = Thorax  Side 1 = left   Time 1 = 3 days;2 = 7 days
Location 2 = Abdomen Side 2 = right       3 = 10 days;4 = 14 days
                                          5 = 18 days;6 = 21 days
                                          7 = 24 days;8 = 28 days

TABLE 6
ANALYSIS OF VARIANCE FOR OUTER WOUND AREA

| | Sum of Squares | Degrees of freedom | Mean Square | F | Tail Prob. | Greenhouse Geisser Prob. |
|---|---|---|---|---|---|---|
| GROUP | 69.62506 | 3 | 23.20835 | 0.28 | 0.8382 | |
| 1-st Covar | 99.18363 | 1 | 99.18363 | 1.20 | 0.2991 | |
| 2-nd Covar | 24.51602 | 1 | 24.51602 | 0.30 | 0.5980 | |
| All Covariates | 148.56050 | 2 | 74.28025 | 0.90 | 0.4378 | |
| 1 Error | 826.98288 | 10 | 82.69829 | | | |
| Loc | 845.24422 | 1 | 845.24422 | 22.57 | 0.0008 | |
| Lg | 126.69419 | 3 | 42.23140 | 1.13 | 0.3839 | |
| 1-st Covar | 10.19168 | 1 | 10.19168 | 0.27 | 0.6133 | |
| 2-nd Covar | 5.66904 | 1 | 5.66904 | 0.15 | 0.7054 | |
| All Covariates | 30.99091 | 2 | 15.49545 | 0.41 | 0.6720 | |
| 2 Error | 374.52801 | 10 | 37.45280 | | | |
| Side | 0.29889 | 1 | 0.29889 | 0.03 | 0.8702 | |
| SG | 34.27186 | 2 | 11.42395 | 1.07 | 0.4037 | |
| 1-st Covar | 23.66999 | 1 | 23.66999 | 2.22 | 0.1667 | |
| 2-nd Covar | 0.02218 | 1 | 0.02218 | 0.00 | 0.9645 | |
| All Covariates | 27.04845 | 2 | 13.52422 | 1.27 | 0.3223 | |
| 3 Error | 106.41888 | 10 | 10.64189 | | | |
| LS | 8.78597 | 1 | 8.78597 | 5.57 | 0.0400 | |
| LSG | 47.01720 | 3 | 15.67240 | 9.93 | 0.0024 | |
| 1-st Covar | 24.39680 | 1 | 24.39680 | 15.46 | 0.0028 | |
| 2-nd Covar | 0.57436 | 1 | 0.57436 | 0.36 | 0.5598 | |
| All Covariates | 24.39697 | 2 | 12.19848 | 7.73 | 0.0093 | |
| 4 Error | 15.78181 | 10 | 1.57818 | | | |
| Time | 14498.88714 | 7 | 2071.26959 | 153.25 | 0.0000 | 0.0000 |
| TG | 119.76275 | 21 | 5.70299 | 0.42 | 0.9862 | 0.8902 |
| 5 Error | 1135.29751 | 84 | 13.51545 | | | |
| LT | 449.74928 | 7 | 64.24990 | 8.55 | 0.000 | 0.0005 |
| LTG | 62.82278 | 21 | 2.99156 | 0.40 | 0.9903 | 0.9097 |
| 6 Error | 630.86037 | 84 | 7.51024 | | | |
| ST | 16.04296 | 7 | 2.29185 | 1.66 | 0.1288 | 0.1643 |
| STG | 45.22903 | 21 | 2.15376 | 1.56 | 0.0785 | 0.1215 |
| 7 Error | 115.63714 | 84 | 1.37663 | | | |
| LST | 4.21439 | 7 | 0.60206 | 0.34 | 0.9353 | 0.8080 |
| LSTG | 51.47539 | 21 | 2.45121 | 1.37 | 0.1588 | 0.2351 |
| 8 Error | 150.52793 | 84 | 1.79200 | | | |
| Error | Epsilon Factors for Degrees of Freedom Adjustment | | | | | |

Statistical analysis as above shows this to be significant for the systemic group (group 4 from FIG. 2) as opposed to the control.

Further analysis of the data shows systemic treatment or a combination of systemic and topical treatment with the omental CMFr material appears to increase the rate of wound closure, especially during the third and fourth weeks of healing in comparison to the controls. An increase of up to 124% of the normal value was obtained.

The mean values of wound area in $cm^2$ [e.g. obtained by raising the square root values in Table I to the square power] were converted into their logarithmic form (i.e. log of wound area). The period of the wound healing experiment was divided into four weeks. Data for the 1st week were obtained from days 1, 3 and 7, 2nd week from days 7, 10, and 14, 3rd week from days 14, 18, and 21, and 4th week from days 21, 24, and 28. The wound area for day 1 was taken as 16 $cm^2$ which is the size of the original wound.

The rate of wound closure was estimated from the slope produced by linear regression of the log (wound area) as a function of time (in days). Correlation coefficients for each regression were excellent with values ranging in most cases from 0.9500 to 0.998. The results are shown in Table 7. The means rates (i.e. from the sum of all sites) for each treatment group (i.e., control, topical, etc.) are shown also in Table 7 and plotted in FIG. 4. This figure also contains the per cent relative increase or decrease in mean rates of wound closure for each treatment group as a function of time.

In comparing the systemic third week results against the control a statistically significant p value of 0.089 is obtained (student T test). In comparing the topical and systemically treated 3rd week results against the control a statistically significant p value of 0.0532 is obtained. It is more difficult to prove significance for the fourth week of treatment due to the large standard deviation so here the mean value is relied on.

As for topical against the control the p value is 0.07 for the second week. Here it is seen there is an actual slowing of wound healing and then a benefit for wound healing in the third week.

Unexpected results show systemic use of CMFr improves epithelial wound healing time with the faster formation of scar as shown.

The omental material can be utilized from various mammalian sources as well, alone and in various combinations of fractions. This wound healing effect should not be strictly limited to dogs but it is obvious it could pertain to other mammals as well.

This omental material HxCMFr or CMFr may also be useful in skin-care products to promote healing of cuts, abrasions and sores.

This unexpected speeding of epithelialization should enhance the rate of autologous skin graft "take" and lead to faster healing of surgical and other skin wounds.

Skin Grafts

The veterinary literature indicates that only about 20% of a full thickness skin graft is likely to survive. Skin grafts depend for survival on development of a blood supply, and if this can be augmented, increased survival can be expected. Percentage survival can be readily determined by measuring the size of the wound margin before and after healing. Any wound surface in an area of graft loss is covered by wound contraction which pulls in the edges of the original wound. Two findings emerged from this experiment. First there appeared to be no significant difference between groups.

TABLE 7

RATES OF WOUND CLOSURE ESTIMATED BY REGRESSION FROM THE DATA OF TABLE I

| Week | Site | Control | Topical | Topical and Systemic | Systemic |
|---|---|---|---|---|---|
| 1st | LT** | 6.25 | 9.42 | 7.92 | — |
|  | RT | 7.03 | 7.10 | 6.71 | 8.67 |
|  | LL | 7.05 | 7.35 | 7.92 | 8.57 |
|  | RL | 8.35 | 6.67 | 10.85 | 7.85 |
|  |  | 7.17 | 7.63 | 8.35 | 8.36 |
|  |  | (±0.75)*** | (±1.05) | (±1.52) | (±0.36) |
| 2nd | LT | 12.86 | 7.90 | 13.10 | 11.94 |
|  | RT | 16.36 | 11.01 | 11.91 | 13.10 |
|  | LL | 11.29 | 11.95 | 13.41 | 10.90 |
|  | RL | 10.70 | 9.90 | 9.79 | 13.64 |
|  |  | 12.80 | 10.19 | 12.05 | 12.39 |
|  |  | (±2.2) | (±1.50) | (±1.42) | (±1.05) |
| 3rd | LT | 3.50 | 6.25 | 4.56 | 5.21 |
|  | RT | — | 5.51 | 11.85 | 11.52 |
|  | LL | 4.95 | 12.56 | 14.64 | 8.51 |
|  | RL | 6.12 | 6.13 | 12.54 | 15.01 |
|  |  | 4.85 | 7.61 | 10.89 | 10.06 |
|  |  | (±1.07) | (±2.87) | (±3.8) | (±3.62) |
| 4th | LT | 12.67 | 21.56 | 11.94 | 22.83* |
|  | RT | 9.33 | 8.63 | 13.04 | 6.97 |
|  | LL | 9.93 | — | 16.68 | 38.66 |
|  | RL | 39.00 | 16.36 | 43.66 | 46.00 |
|  |  | 17.70 | 19.50 | 21.33 | 28.61 |
|  |  | (±12.34) | (±5.3) | (±13.01) | (±15.04) |

*Estimated from data of days 18 and 24.
**LT = Left Thoracic; RT = Right Thoracic; LL = Left Lumbar
***Mean ± standard deviation The second finding is probably more important and indicates the wide variation in percentage survival of grafts between dogs within a single group. In the control wounds, survival ranged from 98% to 40%. This is indicative of the tremendous problems that were encountered in protecting the grafts against external influences, movement, friction against the bandage, self mutilation by the dogs, etc. Accordingly, negative results should not prove that an angiogenic response was not present (See Table 8).

Histopathology

Biopsy samples were obtained by skin punch biopsy of each wound on days 7, 14, 21, and 28. All specimens included original skin, wound edge and regenerating tissue. The specimens were fixed in formaldehyde, paraffin embedded and stained with hematoxylin and eosin. Each section was scored for new vessel formation, degree of fibroplasia and degree of inflammation. Each parameter was given a score of 1+ = mild, 2+ = moderate or 3+ = severe. Results are tabulated in table 9. The scores were lowest in the group treated with triglycerides. No differences were seen in the other 3 treatment groups.

TABLE 8

SURVIVAL OF FULL THICKNESS SKIN GRAFTS

|  | Dog | Side | Original Size | Final Size | % of Original Size | Average |
|---|---|---|---|---|---|---|
| Control | A | R | 1291 | 884 | 68 | 61 |
|  |  | L | 1575 | 627 | 40 |  |
|  | B | R | 2119 | 973 | 46 |  |
|  |  | L | 2145 | 982 | 46 |  |
|  | C | R | 2209 | 1152 | 52 |  |
|  |  | L | 1978 | 1041 | 53 |  |
|  | D | R | 1920 | 1570 | 82 |  |
|  |  | L | 1953 | 1911 | 98 |  |
| Topical Cat | E | R | 2198 | 862 | 39 | 34 |
|  |  | L | 1837 | 915 | 50 |  |

TABLE 8-continued
SURVIVAL OF FULL THICKNESS SKIN GRAFTS

| | Dog | Side | Original Size | Final Size | % of Original Size | Average |
|---|---|---|---|---|---|---|
| | F | R | 2103 | 519 | 25 | |
| | | L | 2313 | 559 | 23 | |
| Topical | G | R | 2140 | 885 | 41 | 58 |
| Bovine | | L | 1299 | 852 | 66 | |
| | I | R | 1894 | 1131 | 60 | |
| | | L | 1895 | 1202 | 63 | |
| T & S | H | R | 2513 | 1192 | 47 | 62 |
| Cat | | L | 2154 | 1044 | 48 | |
| | J | R | 2391 | 2052 | 86 | |
| | | L | 2063 | 1390 | 67 | |
| T & S | K | R | 1816 | 717 | 39 | 50 |
| Bovine | | L | 2231 | 1640 | 74 | |
| | L | R | 2073 | 851 | 41 | |
| | | L | 2377 | 1041 | 44 | |
| Systemic | M | R | 1880 | 1108 | 59 | 51 |
| Cat | | L | 1640 | 1279 | 78 | |
| | N | R | 2052 | 691 | 34 | |
| | | L | 2138 | 701 | 33 | |
| Systemic | O | R | 2655 | 1582 | 60 | 46 |
| Bovine | | L | 2373 | 1039 | 44 | |
| | P | R | 1635 | 535 | 33 | |
| | | L | 1470 | 667 | 45 | |
| Topical | R | R | 2095 | 1251 | 60 | 74 |
| T.G. | | L | 2027 | 1223 | 60 | |
| Cat | S | R | 1960 | 1848 | 94 | |
| | | L | 1547 | 1237 | 80 | |
| Topical | T | R | 2237 | 678 | 30 | 32 |
| T.G. | | L | 1767 | 584 | 33 | |
| Bovine | U | R | 1575 | 445 | 28 | |
| | | L | 1959 | 678 | 35 | |

TABLE 9
Histopathological assessment of wound healing.

| Treatment group | Dog | | New vessel formation | Fibroplasia | Acute inflammation |
|---|---|---|---|---|---|
| Group control | A | | 2+ | 2+ | 2+ |
| | B | | 2+ | 2+ | 2+ |
| | C | | 2+ | 2+ | 2+ |
| | D | | 2+ | 2+ | 1+ |
| | | Total | 8 | 8 | 7 |
| Group topical | E | | 2+ | 2+ | 2+ |
| | F | | 2+ | 2+ | 1+ |
| | G | | 2+ | 2+ | 2+ |
| | I | | 1+ | 2+ | 1+ |
| | | Total | 7 | 8 | 6 |
| Group Topical & systemic | H | | 1+ | 2+ | 1+ |
| | J | | 2+ | 2+ | 2+ |
| | K | | 1+ | 1+ | 1+ |
| | L | | 2+ | 2+ | 2+ |
| | | Total | 6 | 7 | 6 |
| Group systemic | M | | 2+ | 2+ | 1+ |
| | N | | 2+ | 2+ | 2+ |
| | O | | 2+ | 2+ | 2+ |
| | P | | 2+ | 2+ | 2+ |
| | | Total | 8 | 8 | 7 |
| Group | R | | 1+ | 1+ | 2+ |
| Triglyceride | S | | 1+ | 2+ | 1+ |
| | T | | 1+ | 2+ | 2+ |
| | U | | 1+ | 1+ | 2+ |
| | | Total | 4 | 6 | 7 |

1+ = mild
2+ = moderate
3+ = severe

EXAMPLE II

The CMFr was also found to have an anti-bacterial effect as in the following test by Liberco Testing Inc., 123 Hawthorne Street, Roselle Park, N.J. 07204 on feline CMFr:

Method of Assay

U.S.P. XXI Antimicrobial Preservative Effectiveness Page 1151.

| Microbial Challenge Test | ATCC # |
|---|---|
| Staphylococcus Aureus | 6538 |
| Pseudomonas Aeruginosa | 9027 |
| Escherichia Coli | 8739 |
| Candida Albicans | 10231 |
| Aspergillus Niger | 16404 |

The bacteria employed in this study were maintained as broth cultures and the molds were grown on agar slants. 0.1 ml. of a 24 hour broth culture of the test bacteria and 0.1 ml. of 100 ml. of a washing of an agar slant were added to 20 ml. of the sample and well mixed. The samples were stored at room temperature for the entire test period. After storage for 2 days, 1 week, 2 weeks, 3 weeks and 4 weeks a portion of the incubated sample was removed and plated by the serial dilution method. The bacteria were plated on tryptic soy agar with letheen and incubated for 48 hours at 35° C. Yeast and molds were plated on potatoe dextrose agar with letheen and incubated at room temperature for 1 week. The plates were examined for survivors and the percent reduction, against the original number of organisms added, was calculated.

At the same time the test was set up, 0.1 ml. of the test organisms were added to 20 ml. of sterile peptone water. This was immediately plated out to determine the number of organisms added to the sample. This is the culture control.

RESULTS:

| | S. AUREUS | P. AERUGINOSA | E. COLI | C. ALBICANS | A. NIGER |
|---|---|---|---|---|---|
| 0 HOUR COUNT/ML. | 270,000 | 320,000 | 220,000 | 300,000 | 140,000 |
| 2 DAYS COUNT/ML. | <10 | >30,000 | <10 | >30,000 | 120 |
| % REDUCTION | 99.99+ | <90.62 | 99.99+ | <90.00 | 99.91 |
| 1 WEEK COUNT/ML. | 35 | >300,000 | <10 | <10 | 35 |
| % REDUCTION | 99.99 | 0 | 99.99+ | 99.99+ | 99.97 |
| 2 WEEKS COUNT/ML. | <10 | 23,000 | <10 | <10 | <10 |
| % REDUCTION | 99.99+ | 92.81 | 99.99+ | 99.99+ | 99.99+ |
| 3 WEEKS COUNT/ML. | <10 | <10 | <10 | <10 | <10 |
| % REDUCTION | 99.99+ | 99.99+ | 99.99+ | 99.99+ | 99.99+ |
| 4 WEEKS COUNT/ML. | <10 | <10 | <10 | <10 | <10 |
| % REDUCTION | 99.99+ | 99.99+ | 99.99+ | 99.99+ | 99.99+ |

What is claimed is:

1. Method for enhanced wound epithelialization in mammals having epithelial wounds which comprises:
   treating epithelial wounds systemically or topically with pharmacologically active doses of mammalian omental lipid fractions capable of promoting angiogenic activity and comprising ganglioside.

2. Method of claim 1 wherein the pharmacologically active angiogenic material further comprises triglyceride.

3. Method of claim 1 further comprising an anti-bacterial effect.

4. Method of claim 3 further comprising a fungicidal effect.

5. Method for enhanced wound epithelializaiton in mammals having epithelial wounds which comprises:
   treating epithelial wounds systemically or topically with pharmacologically active doses of mammalian omental lipid fractions capable of promoting angiogenic activity and consisting essentially of lipids comprising triglyceride.

6. Method of claim 1, 2 or 5 wherein the pharmacologically active angiogenic omental lipid fraction is obtained by extraction with at least one organic solvent.

7. Method of claim 6 wherein the extraction is a chloroform-methanol extraction.

8. Method of claim 7 wherein the pharmacologically active lipid fraction is a hexane extract of the chloroform-methanol fraction.

9. Method of claim 1, 2 or 5 wherein the pharmacologically active angiogenic omental lipid fraction is a supercritical gas extract of omentum.

10. Method of claim 1, 2, or 5 for treatment of autologous skin grafts.

11. Composition from mammalian omentum for enhancing wound healing and epithelialization comprising a mammlaian omental lipid fraction consisting essentially of isolated ganglioside.

12. Composition from mammalian ometum for enhancing wound healing and epithelialization comprising a mammalian omental lipid fraction wherein the lipid material comprises ganglioside and triglyceride.

13. Composition of claim 12 wherein the lipid material comprises triglyceride.

* * * * *

REEXAMINATION CERTIFICATE (1278th)
United States Patent [19]
Catsimpoolas et al.

[11] B1 4,767,746

[45] Certificate Issued    May 8, 1990

[54] METHOD FOR ENHANCEMENT OF HEALING OF EPITHELIAL WOUNDS IN MAMMALS

[75] Inventors: Nicholas Catsimpoolas, Newton Centre, Mass.; Robert S. Sinn, New York, N.Y.

[73] Assignee: Angio-Medical Corporation, New York, N.Y.

Reexamination Request:
No. 90/001,660, Dec. 7, 1988

Reexamination Certificate for:
Patent No.: 4,767,746
Issued: Aug. 30, 1988
Appl. No.: 805,206
Filed: Dec. 4, 1985

[51] Int. Cl.$^5$ .............. A61K 31/70; A61K 31/715; A61K 31/20
[52] U.S. Cl. ........................ 514/25; 514/54; 514/558; 424/95; 424/DIG. 13
[58] Field of Search ................ 514/25, 54, 558; 424/95, DIG. 13

[56] References Cited

PUBLICATIONS

J. Rabinowitz, et al., "Lipid Composition and Biosynthesis of Human Omental Tissue", Lipids 13: 317-322, 1978.

Guido Tettamanti et al., "The Fate of Exogenously Administered Brain Gangliosides", Gangliosides in Neurological and Neuromuscular Function, Development, and Repair, pp. 225-240 (1981).

A. Gorio et al., "Ganglioside Treatment in Experimental Diabetic Neuropathy", Gangliosides in Neurological and Neuromuscular Function, Development, and Repair, pp. 259-266 (1981).

G. Pozza et al., "The Effect of Ganglioside Administration in Human Diabetic Peripheral Neuropathy", Gangliosides in Neurological and Neuromuscular Function, Development, and Repair, pp. 253-257 (1981).

Alfredo Gorio et al., "Neuritogenesis and Regeneration in the Nervous System: An Overview of the Problem and on the Promoting Action of Gangliosides", Advances in Experimental Medicine and Biology, vol. 174, pp. 465-473 (1984).

G. Toffano et al., "Effects of Gangliosides on the Functional Recovery of Damaged Brain", Advances in Experimental Medicine and Biology, vol. 174, pp. 475-488 (1984).

Stephen E. Karpiak, "Exogenous Gangliosides Enhance Recovery from CNS Injury", Advances in Experimental Medicine and Biology, vol. 174, pp. 489-497 (1984).

Alfredo Gorio et al., "Ganglioside Treatment of Genetic and Alloxan-Induced Diabetic Neuropathy", Advances in Experimental Medicine and Biology, vol. 174, pp. 549-564 (1984).

Walter G. Bradley, "Double-Blind Controlled Trial of Purified Brain Gangliosides in Amyotrophic Lateral Sclerosis and Experience with Peripheral Neuropathies", Advances in Experimental Medicine and Biology, vol. 174, pp. 565-573 (1984).

Steven H. Horowitz, "Ganglioside (Cronassial) Therapy in Diabetic Neuropathy", Advances in Experimental Medicine and Biology, vol. 174, pp. 593-600 (1984).

E. Malizia et al., "Organic Glue Neuropathies: Epidemiology, Clinical Investigation and Therapy of 100 Cases", New Toxicology for Old Arch. Toxicol., Suppl. 5, 103-104 (1982).

G. Ferrari et al., "Gangliosides Enhance Neurite Outgrowth in PC12 Cells", Developmental Brain Research, vol. 8, pp. 215-221 (1983).

M. Rapport, "Introduction to the Biochemistry of Gangliosides", Gangliosides in Neurological and Neuromuscular Function, Development, and Repair, pp. xv-xix, (1981).

T. Yamakawa, "Wonders in Glycolipids—A Historical View", Advances in Experimental Medicine and Biology, vol. 174, pp. 3-13 (1984).

Robert K. Yu, "Gangliosides: Structure and Analysis", Advances in Experimental Medicine and Biology, vol. 174, pp. 39-53 (1984).

K. Suzuki, "Gangliosides and Disease: A Review", Advances in Experimental Medicine and Biology, vol. 174, pp. 407-418 (1984).

*Primary Examiner*—John W. Rollins

[57] ABSTRACT

Omental lipid fractions accelerate wound healing especially as to epithelialization in mammals.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-10 and 12 is confirmed.

Claims 11 and 13 are cancelled.

* * * * *